(12) United States Patent
Jedwab et al.

(10) Patent No.: US 10,387,624 B2
(45) Date of Patent: Aug. 20, 2019

(54) INFUSION PUMP WITH GRAPHIC USER INTERFACE

(71) Applicant: NESTEC S.A., Vevey (CH)

(72) Inventors: Michael Jedwab, Lausanne (CH); Simon Picthall, Borex (CH)

(73) Assignee: Nestec S.A., Vevey (CH)

( * ) Notice: Subject to any disclaimer, the term of this patent is extended or adjusted under 35 U.S.C. 154(b) by 280 days.

(21) Appl. No.: 15/116,880

(22) PCT Filed: Feb. 17, 2015

(86) PCT No.: PCT/EP2015/053316
§ 371 (c)(1),
(2) Date: Aug. 5, 2016

(87) PCT Pub. No.: WO2015/124569
PCT Pub. Date: Aug. 27, 2015

(65) Prior Publication Data
US 2016/0350512 A1    Dec. 1, 2016

(30) Foreign Application Priority Data

Feb. 21, 2014  (EP) .................................... 14156067

(51) Int. Cl.
*G06F 19/00* (2018.01)
*G16H 40/63* (2018.01)
(Continued)

(52) U.S. Cl.
CPC ......... *G06F 19/3468* (2013.01); *G05B 15/02* (2013.01); *G06F 3/04847* (2013.01); *G16H 40/63* (2018.01)

(58) Field of Classification Search
None
See application file for complete search history.

(56) References Cited

U.S. PATENT DOCUMENTS 5,643,212 A     7/1997  Courte et al.
2007/0258395 A1* 11/2007 Jollota ............... A61B 5/14532
                                                    370/310
(Continued)

FOREIGN PATENT DOCUMENTS

EP     2311369      4/2011
EP     2410448      1/2012
(Continued)

OTHER PUBLICATIONS

Edgar et al. "User Interface Guidelines—Eclipsepedia" Nov. 2007, printed from the Internet at http://wiki.eclipse.org/User_Interface_Guidelines, 105 pages.
(Continued)

*Primary Examiner* — Eric C Wai
(74) *Attorney, Agent, or Firm* — K&L Gates LLP

(57) ABSTRACT

The present invention relates to an infusion pump (10) having a control unit (5) and a graphical user interface (3) functionally connected to the controller (5), wherein the control unit (5) is designed to receive at least two sensor signals (S1,S2) out of the following group of sensors: cassette presence sensor, door sensor, pressure sensor, air presence sensor, motor sensor, flow rate sensor, wherein the control unit (5) is designed to detect an error state based on the analysis of the at least two supplied sensor signals (S1,S2), wherein the control unit (5) is designed to associate a degree of severity out of at least two degrees of severities (A1,A3) based on the processing of the supplied sensor signals (S1,S2), and wherein the control unit (5) is designed to control a color of the display (1) of the graphical user interface (3) to be displayed, wherein a different color is associated with each degree of severity (A1,A3) as well as with a non-error state (A0).

19 Claims, 2 Drawing Sheets

(51) Int. Cl.
*G05B 15/02* (2006.01)
*G06F 3/0484* (2013.01)
*G05D 7/00* (2006.01)
*G05D 11/00* (2006.01)

(56) References Cited

U.S. PATENT DOCUMENTS

| | | |
|---|---|---|
| 2009/0270833 A1 | 10/2009 | DeBelser et al. |
| 2012/0079886 A1* | 4/2012 | Beck ................ A61M 5/16854 73/756 |
| 2012/0176394 A1 | 7/2012 | Vik et al. |
| 2013/0281965 A1 | 10/2013 | Kamen et al. |

FOREIGN PATENT DOCUMENTS

| | | |
|---|---|---|
| JP | 01308569 | 12/1989 |
| JP | 05007623 | 1/1993 |
| JP | 07213605 | 8/1995 |
| JP | 2002539898 | 11/2002 |
| JP | 2009516577 | 4/2009 |
| JP | 2011078562 | 4/2011 |
| JP | 2013538652 | 10/2013 |
| WO | 2005011238 | 2/2005 |
| WO | 2009124134 | 10/2009 |
| WO | 2010102069 | 9/2010 |
| WO | 2013141351 | 9/2013 |

OTHER PUBLICATIONS

English Translation of Japanese Office Action dated Dec. 10, 2018 for Patent Application No. 2016-550487.
English translation of JPH057623.

* cited by examiner

INFUSION PUMP WITH GRAPHIC USER INTERFACE

CROSS REFERENCE TO RELATED APPLICATIONS

The present application is a National Stage of International Application No. PCT/EP2015/053316, filed on Feb. 17, 2015, which claims priority to European Patent Application No. 14156067.2, filed Feb. 21, 2014, the entire contents of which are being incorporated herein by reference.

FIELD OF THE INVENTION

The present invention is directed to an infusion pump such as an enteral feeding pump having a control unit and a graphical user interface functionally connected to the control unit. In particular, the invention relates to an infusion pump which provides enhanced status information to a user.

BACKGROUND OF THE INVENTION

The use of infusion pumps to administer solutions to patients is well known in the medical arts. Such infusion pumps are generally used for both enteral and parenteral applications, whereby enteral feeding pumps are used to provide patients with nutrition and medication when they are unable, for a variety of reasons, to eat normally and parenteral respectively intravenous solutions are provided to patients to ensure adequate hydration and to provide needed nutrients, minerals and medication.

These pumps are therefore generally designed such as to administering fluids to a subject in well regulated manner, whereby the infusion pump is used to regulate the amount and rate at which the fluid is delivered from a reservoir to the patient. Typically a tube connected to a supply means such as a reservoir passes through the infusion pump which thus feeds the provided fluid to the patient.

In order to guarantee proper operation of the pumping device, the infusion pumps are generally equipped with sensors for measuring parameters and providing feedback information about the current dosing respectively feeding process. It is further known to provide the pumping device with a user interface in order to display information about the operation of the pumping device and/or to provide feedback information of connected sensors to the user of the pump. Thereby, general information such as temperature, flow rate and amount of administered fluid may be displayed, as well as alarms relating e.g. to a deviation of the sensed parameters from predefined parameters regarding the administering process.

U.S. Pat. No. 5,904,668 for example relates to a pumping device comprising a cassette holding flexible tubing through which fluid can be metered and which is to be inserted into the pumping device. The housing of the device comprises a user interface having a keypad via which a user may input data and commands and a backlighted, dot matrix display for displaying textual messages to the user. At the front side, the pump comprises a pair of LEDs for indicating a normal respectively an abnormal operating condition of the pump. The pump is further equipped with an audible alarm generator.

The known pumping devices suffer the drawback that the feedback information provided by the sensors of the pumping device is usually presented to the user only in text form e.g. by means of a text-output or error code on a dedicated display. In particular with regards to critical information relating to the operational parameters of the pumping device and specifically with regards to error-related information, such presentation is however too complex and may lead to a wrong assessment by the medical personnel operating and/or supervising the administering process by means of the pumping device.

Hence, especially in the field of medical applications, in time-critical situations and/or for use by untrained medical personnel, a quick and easy operable infusion pump is desired, which enables an enhanced and facilitated operation and a convenient presentation of feedback and/or error-related information to the user.

OBJECT AND SUMMARY OF THE INVENTION

Based on the known prior art, the present invention seeks to address the above-described problems. The invention also aims at other objects and particularly the solution of other problems as will appear in the rest of the present description.

In a first aspect, the present invention relates to an infusion pump having a control unit and a graphical user interface (GUI) functionally connected to the controller, wherein the control unit is designed to receive at least two sensor signals out of the following group of sensors: cassette presence sensor, door sensor, pressure sensor, air presence sensor, motor sensor, flow rate sensor, wherein the control unit is designed to detect an error state based on the analysis of the at least two supplied sensor signals, wherein the control unit is designed to associate a degree of severity out of at least two degrees of severities based on the processing of the supplied sensor signals, and wherein the control unit is designed to control a color of the display of the graphical user interface to be displayed, wherein a different color is associated with each degree of severity as well as with a non-error state.

In a preferred embodiment, in addition to the color of the display, the light intensity and/or the illumination frequency of the display may be controlled by the control unit, whereby a different color, light intensity and/or illumination frequency may be associated with each degree of severity as well as with a non-error state.

In a preferred embodiment, the pump is void of any further displays, indicators or status lights such as status LEDs. The graphical user interface comprising the said display thus presents the only display and error indicator of the infusion pump.

According to the invention, the graphic display of the infusion pump is used for providing an enhanced and facilitated feedback information to the user about the operational condition of the pump. Thereby, a compact arrangement of the pump housing is obtained as no additional status lights are to be provided at the pump. Further, the different colored display enables a facilitated understanding of the pump condition even for untrained users or untrained medical personnel.

The infusion pump may be an enteral or parenteral infusion pump. In a preferred embodiment, the infusion pump is an enteral feeding pump adapted for controlling the amount and timing of nutrition and/or medicines delivered to a patient during enteral feeding.

The pump is preferably designed for being connected to a flexible tubing or a cassette holding the flexible tubing through which the nutrition and/or medicines may be administered to a patient. The tubing is preferably connectable to a bag or reservoir containing liquid nutrition and/or medicine. The pump preferably includes a pumping mechanism such as a peristaltic pump adapted to interact with the tubing and designed for conveying liquid through the tubing. Accordingly, the pump is designed for dispensing the content of the supply bag or reservoir in a controlled and accurate manner to a patient.

The pump is preferably designed for providing a continuous and/or an intermittent flow through the tubing associated with the pump, and/or for controlling the dose volume, the dose rate, a time and/or a feeding interval at which the pumping mechanism of the pump is operated.

The pump preferably comprises a plurality of sensors, such as in particular a cassette presence sensor, a door sensor, a pressure sensor, an air presence sensor, a motor sensor, a flow rate sensor, and an upstream and downstream occlusion sensor. The sensors are connected to at least the control unit of the pump. The sensors are designed for providing sensor signals and information to the control unit of the pump.

The cassette presence sensor is preferably designed for providing the control unit of the pump with information regarding the presence of a cassette holding a flexible tubing in a dedicated opening or recess of the housing of the pump.

The door sensor is preferably designed for providing information regarding an opened or closed state of a door of the pump, which closes upon the opening or recess of the housing in which the cassette is to be provided.

The pressure sensor is preferably designed for providing information regarding the fluid pressure present within the tubing and/or the supply reservoir, and/or for providing information regarding the applied pressure of the pumping mechanism onto the tubing.

The air presence sensor is preferably designed for providing information regarding air being present within the flexible tubing.

The motor sensor is preferably designed for providing information regarding the rotational speed and proper functioning of the motor of the pump respectively the motor of the pumping mechanism such as a peristaltic pump.

The flow rate sensor is preferably designed for providing information regarding the flow rate of liquid such as liquid nutrition and/or medicine through the flexible tubing during operation of the pumping mechanism.

The upstream and downstream occlusion sensors are preferably designed for providing information in case the flexible tubing is occluded upstream or downstream of a part of the tubing at which the pumping mechanism of the pump interacts with the tubing.

The graphic user interface of the pump preferably comprises a display with associated buttons and/or a touchscreen for operation of the pump. The display is preferably suitable for displaying text and/or graphic content such as icons. The color of the display is preferably changeable to at least green yellow, red and white.

In a preferred embodiment, the display is designed to change its background color. Therefore, the graphical user interface may comprise a backlight for illumination of the display that is changeable in color. In a preferred embodiment, the display of the graphical user interface comprises an LED backlight module that is designed to illuminate the display at least in the colors green, yellow, red and white. Further, the light intensity and/or the illumination frequency of the display is preferably adaptable.

The display of the graphic user interface is preferably designed for displaying the respective error state in case of an alarm condition graphically or as a text message. The color of the text presented by the display is preferably black. Accordingly, irrespectively of the background color of the display, the user may read the shown letters or text conveniently.

The display of the graphic user interface preferably comprises a minimum size of 20 mm in height and 30 mm in width. The display of the graphic user interface or the graphical user interface as a whole preferably comprises a size respectively surface area which occupies at least 50%, more preferably at least 60%, most preferably at least 75% of the surface area of the side of a housing of the pump, at which side the display is arranged. Accordingly, a relatively large space is provided for giving feedback information of the status of the pump to a user in a facilitated and enhanced way.

The control unit of the pump is designed for analyzing the respective sensor signals provided by the sensors of the pump and for detecting an error state based on the provided sensor signals. Thereby, the control unit may for example comprise information or data storage means in which predefined values or ranges for the respective sensor signals are stored. These predefined ranges or values may be changed by means of a software update and/or a manual user via the graphic user interface. The control unit is thus preferably designed to compare the actual sensor signals with the stored or inputted predefined values or ranges in order to detect a normal respectively an error state.

The control unit is further designed for associating at least two degrees of severities based on the sensor signals and/or the detected state of the respective sensor. The at least two degrees of severities preferably comprise at least a high priority and a low priority alarm condition. In a particular preferred embodiment, the degrees of severities associated by the control unit are a high priority, a medium priority and a low priority alarm condition, as well as a normal or non-error alarm condition.

The control unit is preferably designed for associating the respective degree of severity dependent on the particular type of sensor providing the sensor signal and/or predefined critical ranges and/or critical values of a sensor signal.

The control unit preferably associates a high priority alarm condition to at least a critical sensor signal or an error state provided by the air presence sensor or an upstream or downstream occlusion sensor of the pump. This is in particular the case as the presence of air within the flexible feeding tubing, respectively the occlusion of the tubing upstream or downstream of the pumping mechanism may constitute a high risk for the patient.

The control unit may as well be designed for associating the respective degree of severity dependent on a predefined time period in which a respective critical sensor signal is provided.

In a further mode of the invention, the control unit may be designed for associating the respective degree of severity dependent on an operational mode of the pump such as a battery mode, a mode when the pump is connected to the main supply and/or a simple or an advanced operation mode. The respective modes of the pump will be described in more detail below.

In case the associated alarm condition is a high priority alarm condition, the display color is preferably set to red. In case of a low or medium priority alarm condition, the display color is preferably set to yellow or orange. In case of a low priority alarm condition, the display color may be set to yellow or green. In case of a non-error state, the display color is preferably set to white. During normal operation respectively in a non-error state of the pump, the display illumination in white color is preferably only activated for a predefined time in case a button of the user interface is pressed. In an associated low, medium or high priority alarm condition, the display illumination in the particular predefined color is immediately activated, preferably within 1 second after detection of the alarm condition. The display is then illuminated until the respective alarm condition is overcome respectively not present any longer.

The control unit is designed to adapt a light intensity and/or an illumination frequency of the display in the respective color dependent on the associated degree of severity or the non-error state. The intensity of the colored display is preferably adaptable to be low, medium, high and off. Thereby, the light intensity and/or illumination frequency of the display may as well be set dependent on whether the pump is operated in a battery modus or when connected to the main supply. In case the pump is operated in the battery mode, the light intensity of the colored display is preferably only adjustable to be off, low or medium. The light intensity and/or the illumination frequency of the display is preferably adjusted, e.g. by the control unit, to be in a respectively lower state, e.g. lower light intensity and/or lower illumination frequency, when the pump is operated in the battery mode, than when the pump is connected to the main supply. Thereby, a dedicated sensor may be connected to the control unit which provides information as to whether the pump is connected to the main supply or if the pump is operated in the battery mode.

In particular in an error-state of the pump, the color, the light intensity and/or illumination frequency of the display may be set dependent on the associated degree of severity of the detected error, as well as dependent on whether the pump is operated in its battery mode or if the pump is connected to the main supply.

This arrangement enables the setting of the specific output of the display of the graphical user interface in a non-error state, but also in an error state of the pump, dependent on whether the pump is connected to the main supply or not. Accordingly, an elongated operation of the pump in the battery mode is ensured, even if an error state is detected, while at the same time the enhanced status information to a user of the pump is guaranteed.

In a particular preferred embodiment, the control unit is designed to control the light intensity and/or the illumination frequency of the display to be respectively higher for higher associated degrees of severity. Correspondingly, the light intensity and/or the emission frequency of the colored display may be controlled to be lower for a respective lower associated degree of severity. This may be also the case if the pump is operated in its battery mode. Thereby, the maximum light intensity and/or the maximum illumination frequency in the battery mode of the pump preferably lie below the respective maximum intensity or frequency when the pump is connected to the main supply.

In a preferred embodiment, the pump comprises an ambient light sensor designed for detecting the intensity of the ambient light. Thereby, the control unit of the pump is preferably designed to set the color, the light intensity and/or illumination frequency of the display in the error and/or non-error state dependent on the information provided by the ambient light sensor. Preferably, in an error-state of the pump, the color, the light intensity and/or illumination frequency of the display are set dependent on the associated degree of severity of the detected error, as well as dependent on the information of the ambient light sensor. Thereby, the color, light intensity and/or illumination frequency may be set higher in case the ambient light is brighter than compared to darker ambient light.

In a preferred embodiment, the graphical user interface is designed to support a simple and advanced operation mode. Thereby, in the simple operation mode only a limited set of pump operations is preferably offered to a user of the pump compared to the advanced mode.

Preferably, the display color, the light intensity and/or the illumination frequency of the display is associated respectively controlled to different extent for a respective error state of the pump in the simple and advanced operation mode. For example, for the same error state in the simple operation mode of the pump, a respective higher degree of severity may be associated compared to the advanced operation of the pump.

The infusion pump may as well comprise an audio device connected to the control unit and designed to output and adapt an audible alarm signal such as for example a sequence of tones and pauses dependent on the degree of severity associated by the control unit. Thereby, the frequency and/or intensity and/or duration of the audio alarm signal is preferably controlled dependent on the degree of severity. In a preferred embodiment, the frequency and/or intensity of the audio alarm signal is set higher for a respective higher degree of severity and lower for a respective lower degree of severity.

The control unit is preferably designed to selectively stop the motor of the infusion pump or disable the start of the motor dependent on a detected error and/or dependent on the degree of severity of an alarm condition. In a preferred embodiment, the control unit is designed to stop the motor of the infusion pump or disable the start of the motor when detecting a medium or high priority alarm. Upon a low priority alarm condition detected, the pump is preferably designed to continue any active feeding program uninterrupted.

The pump and/or the control unit of the pump are preferably adapted to output a dedicated error signal together with an indication of the type of error to a remote computer. Thereby, the remote computer may be connected to the pump by means of any suitable wired or wireless connection.

The infusion pump preferably comprises a nurse call interface and/or a patient data management system interface (PDMS) designed for interacting with an external network or device dependent on the degree of severity associated by the control unit. Thereby, the control unit is preferably designed to output a dedicated error signal via the nurse call interface or the PDMS in case the associated degree of severity of the pump is a high or medium priority alarm condition.

BRIEF DESCRIPTION OF THE DRAWINGS

Further features, advantages and objects of the present invention will become apparent for a skilled person when reading the following detailed description of embodiments of the present invention, when taken in conjunction with the figures of the enclosed drawings.

DETAILED DESCRIPTION OF THE FIGURES

Figure 1:
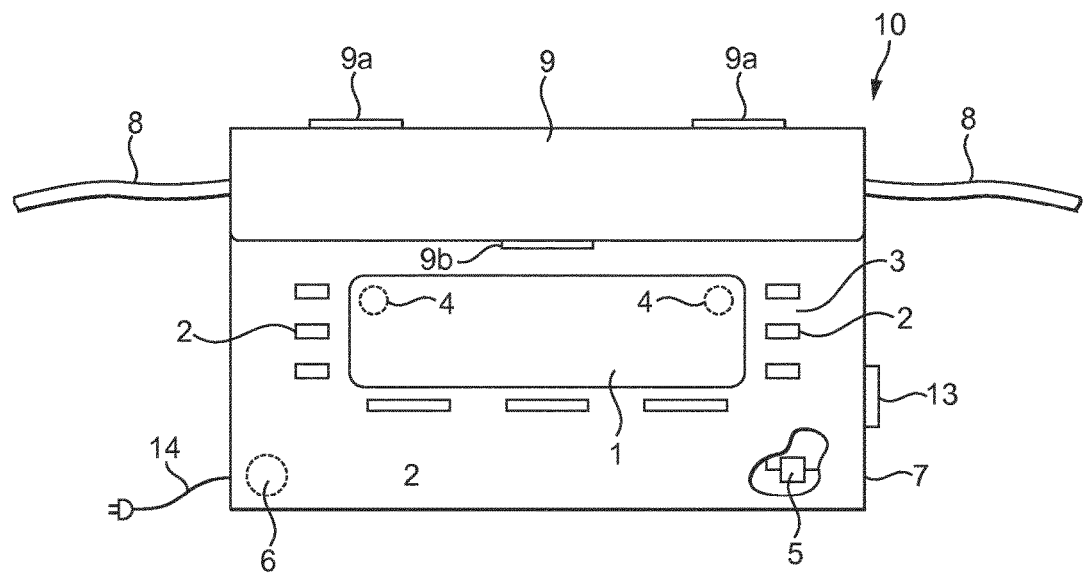
FIG. 1 shows a schematic figure of the pump comprising a graphic user interface according a preferred embodiment of the invention.

FIG. 1 is a schematic figure of a preferred embodiment of the pump device according to the present invention. The pump 10 comprises a housing 7 comprising a graphical user interface 3. The pump further comprises a door 9 which is connected to the housing 7 preferably by means of hinges 9a and can be locked in a closed state as shown in the figure by means of dedicated locking means 9b. In its open state (not shown), the door 9 uncovers a recess or opening in the pump housing into which a flexible tubing 8 or a cassette (not shown) holding the flexible tubing may be inserted.

The pump 10 further comprises a pumping mechanism such as a peristaltic pumping device (not shown) connected to a motor of the pump 10 and designed for interacting with the tubing 8 when being connected to the pump 10 in order to selectively transport fluid through the tubing 8.

The pump 10 is preferably further equipped with a control unit 5 connected to at least a plurality of sensors (see FIG. 2) of the pump 10.

The pump 10 further comprises an audio speaker 6 designed for outputting an audio signal or a series of audio signals and which is connected to the control unit 5. The pump 10 preferably further comprises an interface 13 for connection to a remote computer. The interface 13 may be a nurse call interface and/or a patient data management system interface. The interface 13 is preferably connected to the control unit 5 of the pump. The interface 13 may be suitable for establishing a wired and/or wireless connected to a dedicated remote computer or remote system (11,12).

Furthermore, the pump 10 is preferably equipped with a battery (not shown) and connection means 14 for connecting the pump to the mains.

The graphical user interface 3 of the pump comprises a display 1 and associated buttons 2 and is connected to the control unit 5 of the pump. The buttons 2 are preferably push-buttons that are arranged in close vicinity to the display 1. Instead or as alternative, the display 1 may as well be a touch-display with integrated buttons or dedicated touch-sensors.

The graphical user interface 3 is designed for being used as manual input means by a user of the pump 10, in order to input respectively set operational parameters of the pump 10 such as a desired flow rate, the volume of liquid to be dispensed, the starting and stop time of dispensing, etc.

The display 1 is preferably designed for showing text and/or graphical icons. The display 1 is designed for being illuminated in different colours such as at least white, green, yellow and red. Thereby, the whole surface respectively background of the display may be illuminated in the respective colour, while text or letters are displayed preferably in black colour on the coloured background. The display 1 of the graphical user interface is preferably a colour display suitable for presenting at least the above-identified colours or a black and white text display designed for being illuminated by a provided background light such as one or more LED modules 4. Thereby, the background light is preferably designed for illuminating the black and white text display in the respective colours being at least white, green, yellow and/or red.

The display 1 is designed for changing the colour of the display 1 dependent on information provided by the control unit 5 of the pump 10. Thereby, the display 1 may additionally change the illumination frequency and/or the intensity of the display in the respective colour dependent on information provided by the control unit 5. The display may thus be illuminated in different intensities and at a predefined or adjustable illumination frequency.

The size of the display is preferably at least 20 mm in height and 30 mm in width. More preferably, the display comprises a minimum height of 30 to 50 mm and a minimum width of 40 to 100 mm.

Figure 2:
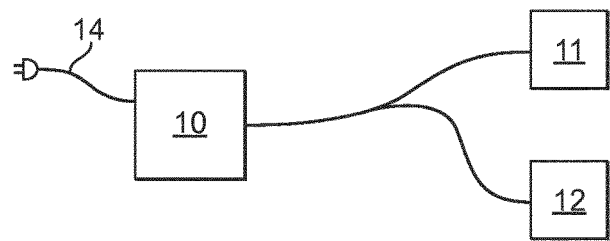
FIG. 2 relates to a system comprising the pump according to the invention being connected to a remote computer and/or a remote system.

FIG. 2 relates to a system comprising the pump 10 according to the invention. As shown in FIG. 2, the pump 10 may be connected to a remote computer 11 and/or a nurse call device 12 by means of a dedicated interface 13. The pump 10 may as well be connected to a patient management system (not shown). When connected to a remote computer 11, a nurse call device 12 or a patient management system, the pump 10 is preferably designed such as to provide information about an error- or non-error state of a particular sensor respectively an associated degree of severity to the connected devices.

Further, dependent on such associated degree of severity, the pump 10 may be designed to indicate an alarm situation of the pump 10 or not. For example, a nurse call output may be sent from the pump 10 to a remote computer 11 or a nurse call device 12 in case of a medium or high priority alarm condition of the pump.

Figure 3:
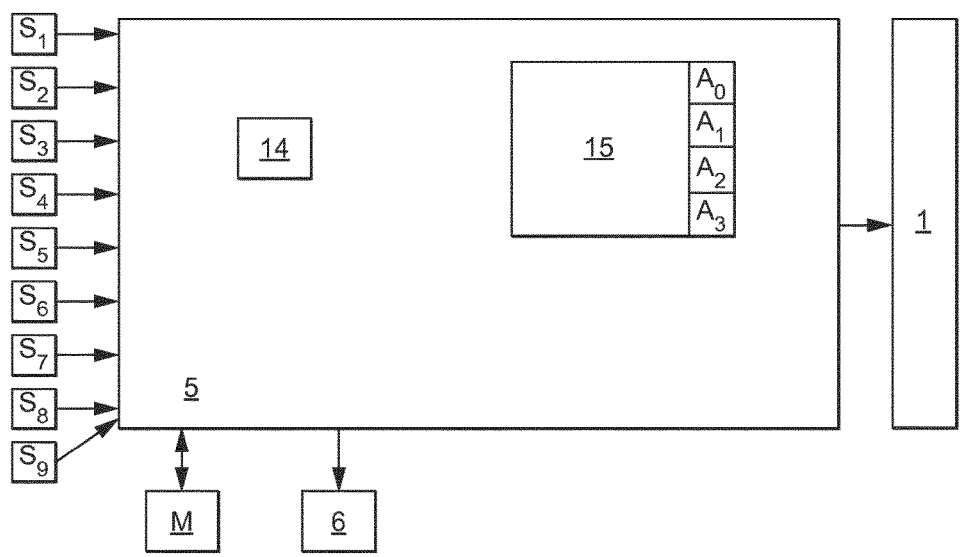
FIG. 3 relates to a block diagram of a preferred embodiment of a control unit of the pump according to the invention.

FIG. 3 relates to a block diagram of the control unit 5 of the pump 10 according to the invention. As shown in FIG. 2, the control unit 5 is connected to various sensors S1, . . . , Sn of the pump 10. Preferably, the control unit 5 is connected to at least a cassette presence sensor S1 for detecting the presence or absence of a cassette and/or tubing being connected to the pump 10, a door sensor S2 for detecting the closure state of the door 9 of the pump, a pressure sensor S3 for providing information regarding the fluid pressure present within the tubing 8 and/or a supply reservoir, and/or for providing information regarding the applied pressure of the pumping mechanism onto the tubing 8, an air presence sensor S4 for providing information whether air is present within the tubing 8, a motor sensor S5 for providing information regarding the activation and speed of the motor of the pumping mechanism, a flow rate sensor S6 for providing information regarding the actual flow rate of liquid through the tubing 8, and an upstream and downstream occlusion sensor S7,S8.

The control unit 5 preferably comprises memory means 14 designed for storing predefined values or ranges for the respective sensor signals S1, . . . , Sn. These predefined values or ranges stored in the memory means 14 preferably relate to reference values for each of the respective sensor information. Accordingly, the control unit 5 may continuously compare the actual values provided by the respective sensors S1, . . . , Sn with reference values predefined or stored within the memory means 14. The reference values are preferably changeable by means of a software update and/or are stored based on information provided by the user via the graphical user interface. For example, the control unit 5 may compare the actually measured flow rate through the tubing with a predefined flow rate that has been entered into the graphical user interface by a user of the pump.

The control unit 5 is further connected to the motor M of the pumping mechanism in order to selectively start and stop the pumping mechanism.

Further, the control unit 5 is connected to the audio device or speaker 6 and the display 1 of the pump 10 in order to control a visual and/or audio output of the pump 10 in response to the information provided by the sensors S1, . . . , Sn.

The control unit 5 preferably further comprises a decision or processing unit 15 which analyses the provided information of the sensors signals S1, . . . , Sn of at least two of the sensors and associates a predefined degree of severity to the provided sensor information. Thereby, besides the non-error or normal state A0, at least two, more preferably three degrees of severity A1,A2,A3 are predefined, relating to a low, a medium and a high priority alarm condition. The respective degree of severity may be associated based on factors such as the particular type of sensor providing an error signal, predefined critical values or ranges of a sensor signal, the presence of a predefined number of error signals from different sensors, and/or a predefined time period in which a respective critical sensor signal is provided.

In a particularly preferred embodiment, a high priority alarm condition A3 is at least associated to a critical or error signal provided by the air presence sensor S4 or an upstream or downstream occlusion sensor S7,S8 of the pump.

Based on the associated degree of severity A1,A2,A3, the control unit 5 may then selectively output a visual and/or audio alarm signal to the display 1 and/or the audio speaker 6 of the pump 10. In addition, the motor M may be controlled to stop dependent on the associated degree of severity, most preferably at least in an associated high priority alarm condition A3. In an associated low priority alarm condition A1, the feeding program is preferably continued.

In particular, the color of the display 1 of the graphical user interface 3 to be displayed is changed for each of the respective associated degrees of severity.

In particular, in a normal or non-error state of associated severity being A0, the display 1 comprises a white or green color. In this non-error state, the illumination of the display is preferably only activated for a predefined time in case a user presses one of the buttons of the graphical user interface.

In the associated priority alarm conditions A1,A2,A3, the display illumination is preferably immediately activated irrespective of whether a user has pressed one of the buttons of the graphical user interface.

In an associated low priority alarm condition A1, the display comprises a yellow color. In an associated high priority alarm condition A3, the display comprises red color. In a medium priority alarm condition A2, the display may comprise a yellow and/or red alarm condition or color different therefrom such as orange color.

In a particular preferred embodiment, a critical information of the downstream or upstream occlusion sensor S7,S8, an error signal of the air presence sensor S4, as well as low charged battery sensed by a provided battery sensor S9 is associated to a high priority alarm condition A3 and consequently leads to an illumination of the display in red color. The detection of an open door by door sensor S2, an absence of the cassette detected by presence sensor S1, an empty reservoir respectively the end of liquid supply detected by e.g. the pressure sensor S3, or a pause of the motor M of the pumping mechanism detected by a dedicated motor sensor S5 is associated to a low and/or medium priority alarm condition A1,A2 and consequently leads to an illumination of the display in yellow or orange color.

In addition to the color of the display 1 being adapted by the control unit 5 based on the associated degree of severity, the control unit 5 may as well change the intensity and/or frequency of illumination of the display 1 in the respective color. Preferably, the intensity of the colored display 1 is set higher with a higher associated priority alarm condition.

In a particular preferred embodiment, the illumination intensity of the respectively colored display is set to at least 50% higher in the low or medium priority alarm condition A1,A2 and 100% higher in the high priority alarm condition A3, compared to a default illumination value in the non-error state of the pump 10.

The pump 10 may further comprise an ambient light sensor in order to detect the intensity of the ambient light and adapt the intensity level of the display 1 at least in a normal non-error condition of the pump to the detected ambient light intensity. Thereby, the color, light intensity and/or illumination frequency of the display 1 may be set higher in case the ambient light is brighter than compared to darker ambient light.

Alternatively to an illumination of the display in the respective color at a predefined illumination frequency for the associated degree of severity, the display may be constantly illuminated in case of an alarm condition.

In a normal operating state or non-error condition A0 of the pump, any illumination of the display 1 such as a white or green colored illumination is generally deactivated after a predefined time, such as for example 5 to 10 seconds, in case none of the buttons of the graphical user interface is pushed.

An alarm condition, in particular a low or medium priority alarm condition A1,A2 may as well be associated as reminder for a maintenance of the pump after a predefined time period.

The graphical user interface 3 is preferably designed to support a simple and advanced operation mode. In the simple operation mode, only a limited set of operations is offered to the user of the pump. The display color, the light intensity and/or the illumination frequency of the display 1 may be associated respectively controlled to different extent for a respective error state of the pump in the simple and advanced operation mode. For example, for the same error state in the simple operation mode of the pump, a respective higher degree of severity may be associated compared to the advanced operation of the pump.

The graphical user interface 3 is preferably further designed to display a corresponding text message indicating the particular error state as detected by the control unit 5. Thereby, the display 1 may further display an instruction or corrective action to be carried out by the user of the pump 1 in order to overcome the alarm condition.

The invention claimed is:

1. An infusion pump having a control unit and a graphical user interface functionally connected to the control unit;
   wherein the control unit is designed to receive at least two sensor signals from at least two sensors selected from the group consisting of: cassette presence sensor, door sensor, pressure sensor, air presence sensor, motor sensor, and flow rate sensor;
   wherein the control unit is designed to detect an error state based on the analysis of the at least two sensor signals;
   wherein the control unit is designed to associate a degree of severity from at least two degrees of severities based on the processing of the at least two sensor signals; and
   wherein the control unit is designed to control a color of a display of the graphical user interface to be displayed, wherein a different color is associated with each degree of severity as well as with a non-error state,
   wherein the graphical user interface is designed to support a simple operation mode and an advanced operation mode, whereby in the simple operation mode only a limited set of pump operations is offered to a user of the pump, wherein the degree of severity associated to a same error state is higher in the simple operation mode than in the advanced operation mode.

2. The infusion pump according to claim 1, wherein the degrees of severity comprise a high priority, a medium priority and a low priority alarm condition.

3. The infusion pump according to claim 1, wherein the control unit is designed for associating the respective degree of severity dependent on the particular type of sensor providing the sensor signal and/or predefined critical ranges and/or critical values of a sensor signal.

4. The infusion pump according to claim 1, wherein the control unit is designed for associating the respective degree of severity dependent on a predefined time period in which a respective critical sensor signal is provided.

5. The infusion pump according to claim 1, wherein the control unit is designed for associating the respective degree of severity dependent on an operational mode of the pump.

6. The infusion pump according to claim 1, wherein the control unit is designed for associating a high priority alarm condition to at least a critical sensor signal or an error state provided by the air presence sensor or an upstream or downstream occlusion sensor of the pump.

7. The infusion pump according to claim 1, wherein the control unit is designed to adapt a light intensity and/or an illumination frequency of a colored display dependent on the associated degree of severity or the non-error state.

8. The infusion pump according to claim 7, wherein the control unit is designed to control the light intensity and/or the illumination frequency of the colored display to be respectively higher for a higher associated degree of severity and lower for a lower associated degree of severity.

9. The infusion pump according to claim 1, wherein the infusion pump comprises an audio device connected to the control unit and designed to output and adapt an audible alarm signal dependent on the degree of severity associated by the control unit.

10. The infusion pump according to claim 1, wherein the control unit is designed to control the graphical user interface to display a respective error state graphically or as a text message.

11. The infusion pump according to claim 1, wherein the color of the display of the graphic user interface is adaptable as being at least red, yellow and/or green.

12. The infusion pump according to claim 1, wherein the control unit is designed to stop a motor of the infusion pump or disable the start of the motor when detecting an error state or dependent on an associated degree of severity.

13. The infusion pump according to claim 1, wherein the control unit is adapted to output a dedicated error signal together with an indication of the type of error to a remote computer.

14. The infusion pump according to claim 1, wherein the infusion pump comprises a nurse call interface and/or a patient data management system interface designed for interacting with an external network or device dependent on the degree of severity associated by the control unit.

15. The infusion pump according to claim 14, wherein the control unit is designed to output a dedicated error signal via the nurse call interface in case the associated degree of severity of the pump is a high or medium priority alarm condition.

16. The infusion pump according to claim 1, wherein the light intensity of the display and/or the illumination frequency is set dependent on whether the pump is operated in its battery modus or connected to the main supply.

17. The infusion pump according to claim 1, wherein the pump comprises an ambient light sensor designed for detecting the intensity of the ambient light and wherein the pump is configured to adapt the intensity level of the display to the detected ambient light intensity.

18. The infusion pump according to claim 1, wherein the pump is an enteral feeding pump.

19. The infusion pump according to claim 1, wherein the infusion pump has at least one configuration selected from the group consisting of: (i) the pump comprises a housing and a door connected to the housing to reversibly cover and uncover a recess and/or opening in the housing, the recess and/or opening configured to receive a flexible tubing inserted into the housing, and wherein the control unit is configured to operate a pumping mechanism to selectively transport a fluid through the flexible tubing; (ii) the display of the graphical user interface is configured to change a background color of the display; (iii) an entire surface of the display of the graphical user interface is illuminated in the selected color associated with one of the each degrees of severity; (iv) the display of the graphical user interface is the only display, indicator and/or status light of the infusion pump; (v) the display of the graphical user interface is deactivated after a predetermined time in a normal operating state and/or the non error state; and (vi) the display of the graphical user interface comprises an LED backlight module.

* * * * *